United States Patent
Podilchuk et al.

(10) Patent No.: US 10,453,570 B1
(45) Date of Patent: Oct. 22, 2019

(54) DEVICE TO ENHANCE AND PRESENT MEDICAL IMAGE USING CORRECTIVE MECHANISM

(71) Applicant: Sonavista, Inc, Warren, NJ (US)

(72) Inventors: Christine I. Podilchuk, Warren, NJ (US); Richard Mammone, Warren, NJ (US)

(73) Assignee: SONAVISTA, INC., Warren, NJ (US)

(*) Notice: Subject to any disclaimer, the term of this patent is extended or adjusted under 35 U.S.C. 154(b) by 0 days.

(21) Appl. No.: 16/190,598

(22) Filed: Nov. 14, 2018

Related U.S. Application Data (60) Provisional application No. 62/680,230, filed on Jun. 4, 2018, provisional application No. 62/690,008, filed on Jun. 26, 2018.

(51) Int. Cl.
| | |
|---|---|
| *G16H 30/40* | (2018.01) |
| *G06T 7/00* | (2017.01) |
| *G06T 7/90* | (2017.01) |
| *G06T 5/00* | (2006.01) |
| *G06K 9/46* | (2006.01) |

(52) U.S. Cl.
CPC ........... *G16H 30/40* (2018.01); *G06T 7/0012* (2013.01); *G06K 9/4661* (2013.01); *G06K 2209/05* (2013.01); *G06T 5/002* (2013.01); *G06T 5/003* (2013.01); *G06T 5/006* (2013.01); *G06T 7/90* (2017.01); *G06T 2207/10004* (2013.01); *G06T 2207/10024* (2013.01); *G06T 2207/10081* (2013.01); *G06T 2207/10088* (2013.01); *G06T 2207/10104* (2013.01); *G06T 2207/10116* (2013.01); *G06T 2207/10132* (2013.01); *G06T 2207/20076* (2013.01); *G06T 2207/20104* (2013.01); *G06T 2207/20201* (2013.01); *G06T 2207/30168* (2013.01)

(58) Field of Classification Search
USPC .......................... 382/103, 128, 254, 275, 155
See application file for complete search history.

(56) References Cited

U.S. PATENT DOCUMENTS

| | | | |
|---|---|---|---|
| 10,311,570 B1 * | 6/2019 | Podilchuk | G06T 7/0014 |
| 2002/0165837 A1 * | 11/2002 | Zhang | G06K 9/623 706/16 |
| 2008/0025592 A1 * | 1/2008 | Jerebko | A61B 6/466 382/132 |

OTHER PUBLICATIONS

Dave Fornell, "How Artificial Intelligence Will Change Medical Imaging", Feb. 24, 2017, Imaging Technology News, Retrieved from Internet at <URL: https://www.itnonline.com/article/how-artificial-intelligence-will-change-medical-imaging>, retrieved on Mar. 12, 2019.*

(Continued)

*Primary Examiner* — Ishrat I Sherali
(74) *Attorney, Agent, or Firm* — Gearhart Law, LLC (57) ABSTRACT

A device to enhance and present a medical image using a corrective mechanism is described. An image analysis application executed by the device captures a digital copy of the medical image displayed on a display device. A flawed photography effect associated with the digital copy is identified by processing the digital copy. Next, the digital copy is enhanced based on the flawed photography effect. Furthermore, the enhanced digital copy can be processed with an artificial intelligence mechanism to generate an annotation. The annotation is associated with a cancer identification. In addition, the enhanced digital copy and the annotation are displayed.

18 Claims, 6 Drawing Sheets

(56) References Cited

OTHER PUBLICATIONS

Taylor Kubota, "Deep learning algorithm does as well as dermatologists in identifying skin cancer", Jan. 25, 2017, Stanford News, Retrieved from Internet at <URL: https://news.stanford.edu/2017/01/25/artificial-intelligence-used-identify-skin-cancer/>. Retrieved on Mar. 12, 2019.*
Dong et al., 2015, Research on an Improved Medical Image Enhancement Algorithm Based on P-M Model, Bimedical Engineering Journal, 9, 209-213, Retrieved from Internet at <URL: https://www.ncbi.nlm.nih.gov/pmc/articles/PMC4645970/pdf/TOBEJ-9-209.pdf>, retrieved on Mar. 12, 2019.*
Ishikawa et al., Mar. 16, 2008, "Medical Image Analysis using Mobile Devices", Retrieved from: http://delivery.acm.org/10.1145/1370000/1364005/p1380-ishikawa.pdf?ip=151.207.250.41&id=1364005&acc=ACTIVE%20SERVICE&key=C15944E53D0ACA63%2E4D4702B0C3E38B35%2E4D4702B0C3E38B35%2E4D4702B0C3E38B35&_acm_=1551885094_d3538550d.*
Alex Kendall and Roberto Cipoila, "Geometric loss functions for camera pose regression with deep learning", CVPR 2017, 10 pages.
Dong et al., "Image Super-Resolution Using Deep Convolutional Networks", Jul. 31, 2015, 14 pages.
Ledig et al., "Photo-Realistic Single Image Super-Resolution Using a Generative Adversarial Network", May 25, 2017, 19 pages.
Johnson et al., "Perceptual Losses for Real-Time Style Transfer and Super-Resolution", Mar. 27, 2016, 18 pages.
Shi et al., "Real-Time Single Image and Video Super-Resolution Using an Efficient Sub-Pixel Convolutional Neural Network", Sep. 23, 2016, 10 pages.

* cited by examiner

DEVICE TO ENHANCE AND PRESENT MEDICAL IMAGE USING CORRECTIVE MECHANISM

CLAIM OF PRIORITY

This application claims priority to U.S. Application Ser. No. 62/680,230 filed on Jun. 4, 2018 and to U.S. Application Ser. No. 62/690,008 filed on Jun. 26, 2018, the contents of which are herein incorporated by reference in its entirety.

FIELD OF THE EMBODIMENTS

The field of the embodiments relate to a device to enhance and present a medical image using a corrective mechanism. The corrective mechanism may remove a flawed digital photography effect from a digital copy of the medical image prior to processing the digital copy to determine an annotation.

BACKGROUND OF THE EMBODIMENTS

Information exchanges have changed processes associated with work and personal environments. Automation and improvements in processes have expanded the scope of capabilities offered for personal and business data consumption. With the development of faster and smaller electronics, a variety of mobile devices have integrated into daily lives. A modern mobile device includes components to provide variety of services such as communication, display, imaging, voice, and/or data capture, among others. Abilities of the modern mobile device jump exponentially when networked to other resources that provide previously unimagined number of services associated with medical imaging.

Commercial Medical Imaging systems such as ultrasound, x-ray, mammography, computed tomography (CT), magnetic resonance imaging (MRI), positron emission tomography (PET) use proprietary software to protect the manufacturers' intellectual property and regulation compliant storage and communication protocols to ensure patient privacy. Imaging systems are used for detection and diagnosis of medical conditions such as cancer, cardiovascular disease and other diseases of different body parts including but not limited to breast, lungs, musculoskeletal, thyroid, kidney, liver, prostate and other body parts. Third party software applications developers face potential challenges associated with many different software platforms which support the numerous vendors' hardware medical imaging devices.

SUMMARY OF THE EMBODIMENTS

The present invention and its embodiments relate to a device to enhance and present a medical image using a corrective mechanism. The device may be configured to capture a digital copy of the medical image displayed on a display device. Next, a flawed photography effect associated with the digital copy may be identified by processing the digital copy with a computer analysis and correction module (CACM). The digital copy may be enhanced with the CACM based on the flawed photography effect. The enhanced digital copy may be directly displayed for diagnosis or processed with an additional artificial intelligence mechanism such as any a computer assisted diagnosis (CADx) or a computer assisted detection (CADe) system that is available to generate an annotation associated with the enhanced digital copy. The annotation reported may be associated with a cancer identification or other disease state. The annotation may be numeric such as the probability of malignancy. The annotation might be pictorial such as the position of the images' score within a histogram of scores of images that were benign to malignant. The annotation can also be in the form of images such as similar images that were found to contain cancer or be benign under biopsy. In addition, both the enhanced digital copy and the annotation may be displayed.

In another embodiment of the present invention, a mobile device for enhancing and presenting a medical image using a corrective mechanism is described. The mobile device may include a display component configured to accept an input and display an output associated with an image analysis application. A camera component may be configured to capture a digital copy of the medical image in relation to the image analysis application. A memory may be configured to store instructions associated with the image analysis application. A processor may be coupled to the display component, the camera component, and the memory. The processor may execute the instructions associated with the image analysis application. The image analysis application may include a computer assisted correction module (CACM). The CACM may be configured to receive a first digital copy of the medical image from the camera component. The camera component may be configured to capture the first digital copy of the medical image displayed on a display device. Next, a flawed photography effect associated with the first digital copy may be identified by processing the first digital copy. The first digital copy may be enhanced based on the flawed photography effect. Furthermore, the first digital copy may be processed with an artificial intelligence mechanism to generate an annotation. The annotation may include a suspicious label, a not suspicious label, or a follow-up label associated with a cancer identification or identification of another disease state. The first digital copy and the annotation may be displayed on the display component.

In yet another embodiment of the present invention, a method of enhancing and presenting a medical image using a corrective mechanism is described. The method includes receiving a digital copy of the medical image from an image source. Next, a flawed photography effect associated with the digital copy may be identified by processing the digital copy. The digital copy may be enhanced based on the flawed photography effect. Furthermore, the digital copy may be processed with an artificial intelligence mechanism to generate an annotation. The annotation may include a suspicious label, a not suspicious label, or a follow-up label associated with a cancer identification or identification of another disease state. The digital copy and the annotation may next be provided for a presentation.

It is an object of the embodiments of the present invention to enhance a digital copy of a medical image captured by a camera of a mobile device.

It is an object of the embodiments of the present invention to annotate the digital copy associated with a cancer identification.

It is an object of the embodiments of the present invention to detect a flawed photography effect associated with the digital copy.

It is an object of the embodiments of the present invention to remove the flawed photography effect.

It is an object of the embodiments of the present invention to present the enhanced digital copy along with the annotation to a user.

These and other features, aspects and advantages of the present invention will become better understood with reference to the following drawings, description and claims.

DESCRIPTION OF THE PREFERRED EMBODIMENTS

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations may be made thereto.

Figure 1:
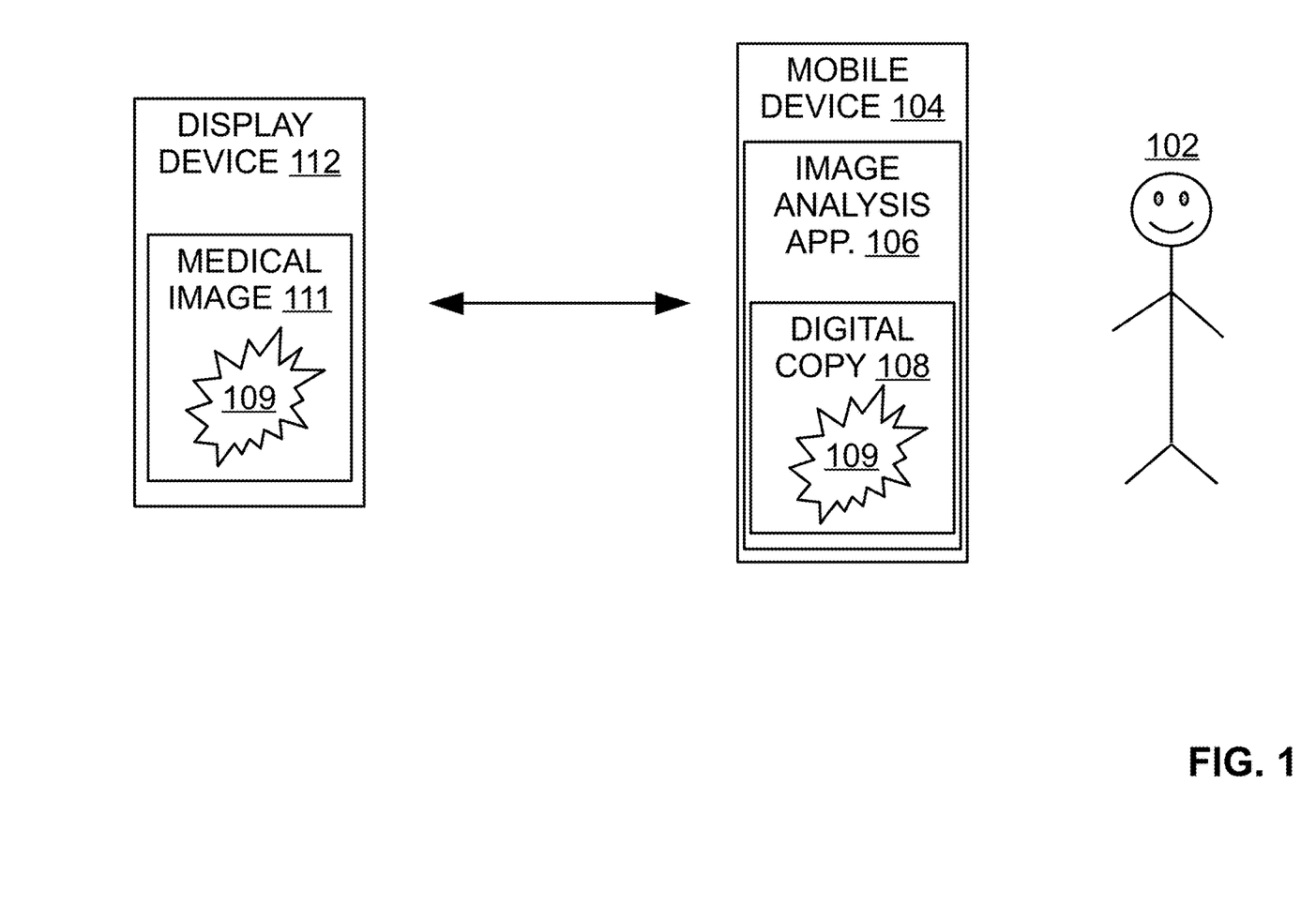
FIG. 1 shows a conceptual diagram illustrating examples of enhancing and presenting a medical image using a corrective mechanism, according to an embodiment of the invention.

FIG. 1 shows a conceptual diagram illustrating examples of enhancing and presenting a medical image using a corrective mechanism. In an example scenario, a mobile device 104 may execute (or provide) an image analysis application 106. The mobile device 104 may include a physical computing device hosting and/or providing features associated with a client application (such as the image analysis application 106). The mobile device 104 may include and/or is part of a smart phone, a tablet based device, and/or a laptop computer, among others. The mobile device 104 may also be a node of a network. The network may also include other nodes such as a display device 112, among others. The network may connect nodes with wired and wireless infrastructure.

The mobile device 104 may execute the image analysis application 106. The image analysis application 106 may capture a digital copy 108 of a medical image 111 displayed on a display device 112. An example of the medical image 111 may include an ultrasound image, a x-ray image, a magnetic resonance imaging (MRI) scan, a computed tomography (CT) scan, and/or a positron emission tomography (PET) scan, among others. The display device 112 may include a monitor associated with a diagnostic system that captures, manages, and/or presents the medical image 111 to a user 102 such as a doctor, a nurse, a technician, a patient, and/or an administrator, among others.

The medical image 111 and the digital copy 108 may include a region of interest (ROI) 109. The ROI 109 may represent a malignant or a benign tumor. Alternatively, the ROI 109 may represent another structure associated with an organ and/or other part of a patient captured in the medical image 111. Alternately the operator can select a region of interest within the digital image or alternatively a computer assisted detection (CADe) module can select the ROI automatically.

The image analysis application 106 may next identify a flawed photography effect associated with the digital copy 108 by processing the digital copy 108 with a computer analysis and correction module (CACM). The CACM may analyze and enhance the digital copy 108 and generate an enhanced version of the digital copy 108. An artificial intelligence (AI) mechanism such as the CACM, a computer assisted diagnosis (CADx), and/or the CADe may be used to process, analyze, and designate the digital copy 108 with an annotation. The AI may be a component of the image analysis application 106. Alternatively, the AI system, such as the CACM, may be a service provided by an external entity such as another application. The flawed photography effect may include number of errors associated with capture and/or processing of the medical image 111 and/or the digital copy 108.

The image analysis application 106 may enhance the digital copy 108 based on the flawed photography effect. For example, the image analysis application 106 may remove the flawed photograph effect such as a glare effect and/or a reflection effect (associated with use of a flash and/or lighting in the vicinity of the medical image 111). The computer analysis might find one or more faults or no faults. If no faults are found the image is passed on to the next step of the diagnostic process. If one or more faults are found by the computer analysis component those faults are corrected by the correction component of the CACM. Next, the digital copy 108 may be processed with the AI mechanism to generate an annotation. The AI mechanism may include a deep learning, a machine vision, and/or a machine learning mechanism, among others based mechanism to process and classify the digital copy 108 and the ROI 109. The annotation may be associated with a cancer identification. For example, the annotation may include a suspicious, a not suspicious, and/or a follow up label. The image analysis application 106 may next display the digital copy 108 and the annotation to the user 102.

Previous example(s) to enhance and present a medical image are not provided in a limiting sense. Alternatively, the image analysis application 106 may perform operations associated with enhancing and presenting the digital copy 108 as a desktop application, a workstation application, and/or a server application, among others. The image analysis application 106 may also be a client interface of a server based application.

The user 102 may interact with the image analysis application 106 with a keyboard based input, a mouse based input, a voice based input, a pen based input, and a gesture based input, among others. The gesture based input may include one or more touch based actions such as a touch action, a swipe action, and a combination of each, among others. The user 102 may also interact with the CACM by use of an augmented reality headset which provides an annotated overlay on top of the screen of the medical image display.

While the example system in FIG. 1 has been described with specific components including the mobile device 104, the image analysis application 106, embodiments are not limited to these components or system configurations and can be implemented with other system configuration employing fewer or additional components.

Figure 2:
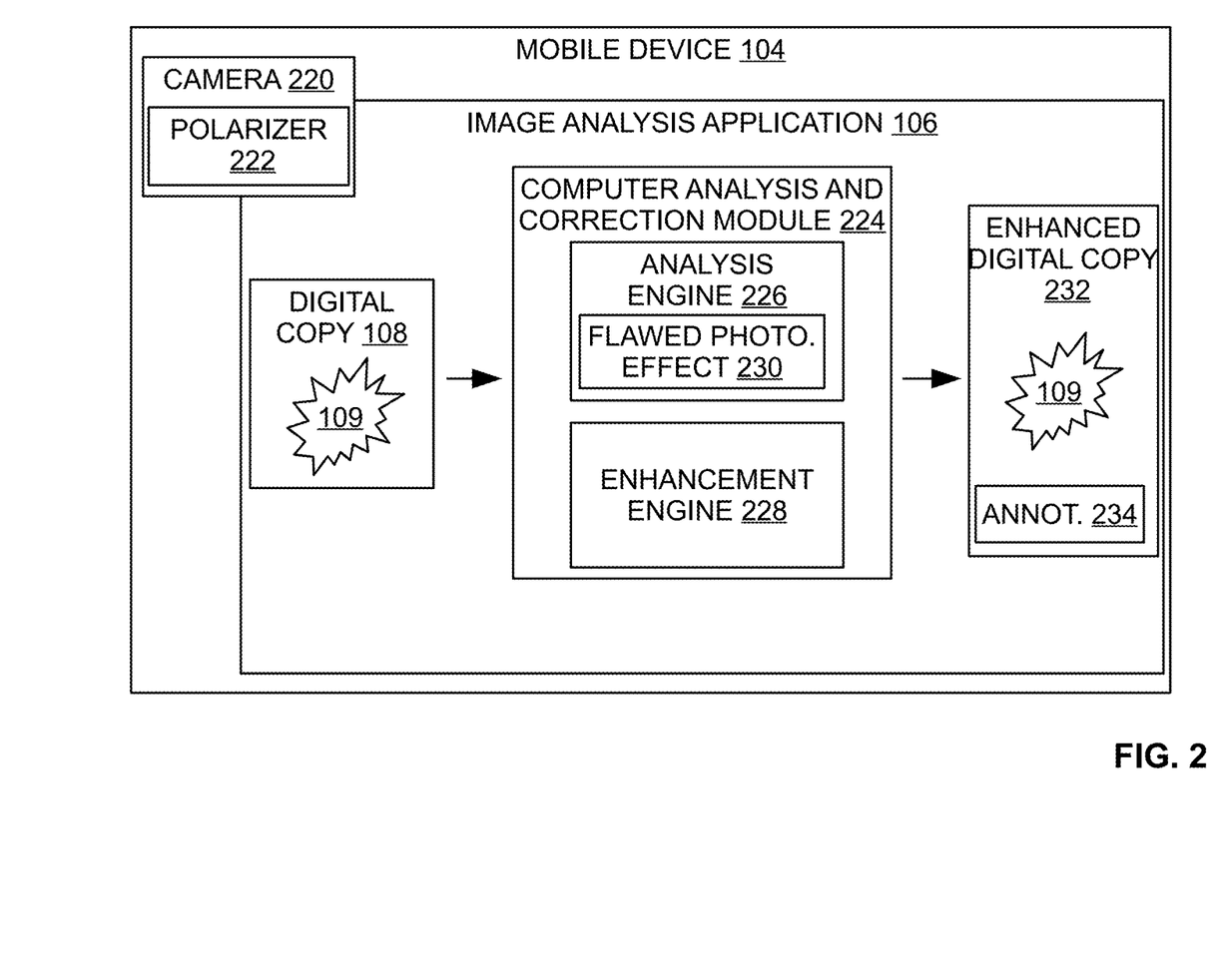
FIG. 2 shows a display diagram illustrating interactions between components of a device that enhances and presents a medical image using a corrective mechanism, according to an embodiment of the invention.

FIG. 2 shows a display diagram illustrating interactions between components of a device that enhances and presents the medical image using a corrective mechanism. In an example scenario, the mobile device 104 may include components such as a camera 220 and a polarizer 222. The polarizer 222 may be attached or integrated to a lens of the camera 220. The polarizer 222 may be rotated to pass only light polarized in a direction perpendicular to a reflected light. As such, the polarizer 222 may absorb a significant proportion of the reflected light. As a result, the polarizer 222 may absorb a glare effect and/or a reflection effect that results from capturing the digital copy 108 from a display device displaying the medical image.

In an example scenario, the image analysis application 106 may process the digital copy 108 to enhance and annotate the digital copy 108 of the medical image. The digital copy 108 may include the ROI 109. The ROI 109 may include a lesion or another structure associated with the organ or other body component that is scanned by the medical image.

The image analysis application 106 may process the digital copy 108 with the CACM 224 to determine a flawed photography effect 230. The flawed photography effect 230 may arise from a number errors associated with capturing the digital copy 108 from the displayed medical image. Furthermore, the flawed photography effect 230 may also be a result of error(s) introduced during the initial capture of the medical image. Identification of the flawed photography effect 230 and an enhancement process to correct error(s) associated with the flawed photograph effect 230 may aid or substantially impact a determination of a correct annotation of the digital copy 108. A likelihood of determining the correct annotation may also improve in response to identification of the flawed photography effect 230 and enhancement of the digital copy 108 based on the flawed photography effect 230.

In an example scenario, an analysis engine 226 of the CACM 224 may process the digital copy 108 to identify the flawed photography effect 230. The analysis engine 226 may analyze non-image information associated with the digital copy 108 to identify the flawed digital effect 230. The non-image information may include a flash information, a focal length, a shutter speed, a camera model information, an aperture setting, and/or a capture date and time information, among others. For example, the analysis engine 226 may determine the focal length of the camera in an incorrect configuration as the flawed photography effect 230. In another example scenario, the shutter speed may be determined to be not optimal in relation to ambient lighting. In response, an enhancement engine 228 (of the CACM 224) may enhance the digital copy 108 to remove and/or alleviate the flawed digital effect 230. For example, the enhancement engine 228 may lighten or darken the digital copy 108 to alleviate an underexposure or an overexposure (determined as the flawed digital effect 230) to produce an enhanced digital copy 232.

The analysis engine 226 may also analyze image characteristic(s) of the digital copy 108 to identify the flawed photography effect 230. The image characteristic(s) may include an orientation, image blur, a red-eye detection, a blur, a color balance, an exposure, and/or a noise information, among others associated with the digital copy 108. Upon identifying the flawed photography effect, the enhancement engine 228 may process the digital copy 108 to remove the flawed photography effect 230. For example, the enhancement engine 228 may remove the flawed photography effect 230 by re-orienting the digital copy 108, removing a red-eye effect, and/or adjusting a color of the digital copy 108, among other operations to produce the enhanced digital copy 232.

Next, the CACM diagnosis module 224 may further process the enhanced digital copy 232 with an AI mechanism to determine an annotation 234 The AI mechanism my include a deep learning, a neural network, a machine vision, and/or a machine learning mechanism, among others. The AI mechanism may identify the ROI 109 and classify the ROI 109 with the annotation 234. The annotation 234 may include a cancer identification. The annotation 234 may include a suspicious label, a not suspicious label, and/or a follow-up label, among others.

Figure 3:
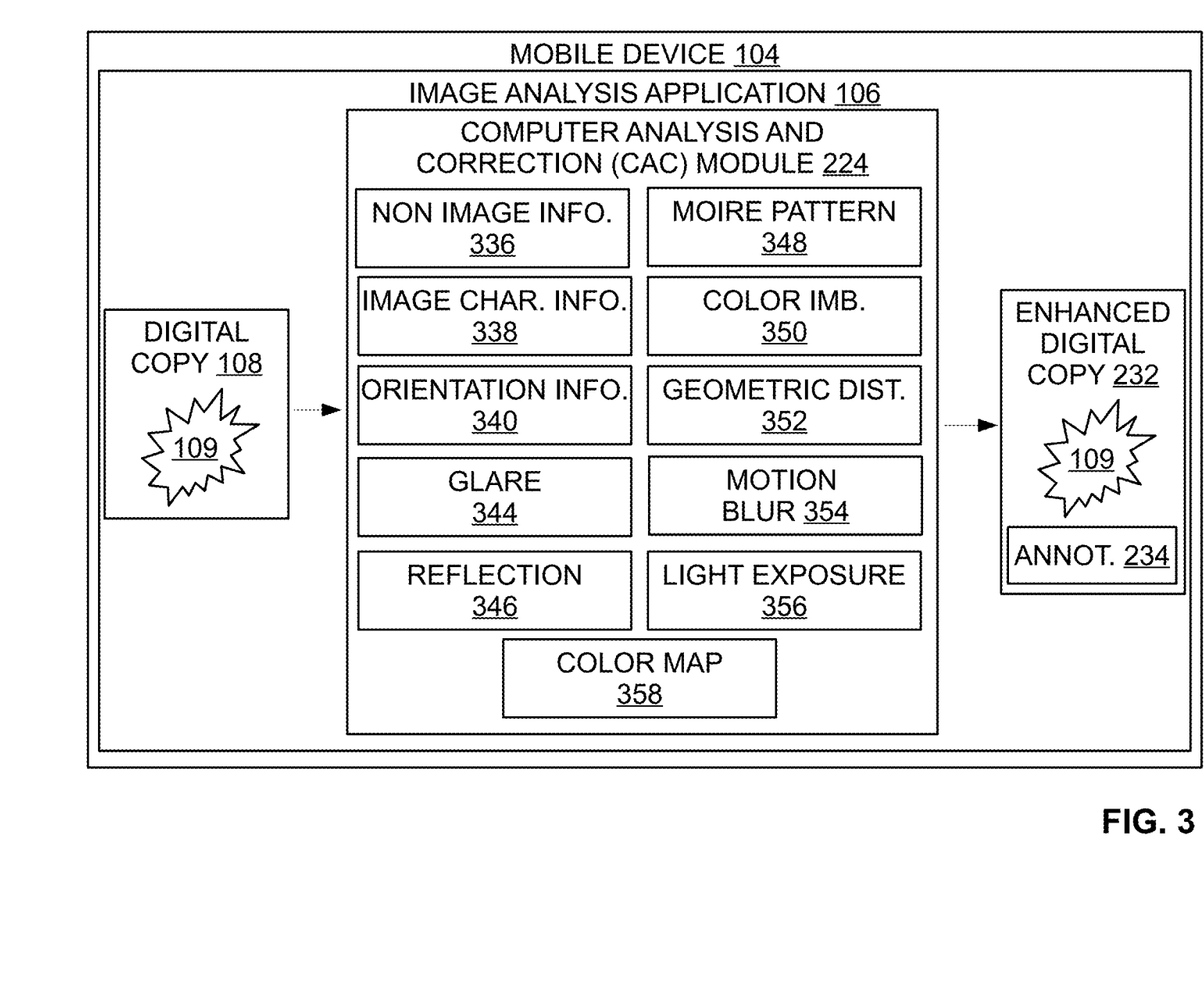
FIG. 3 shows a display diagram illustrating a corrective mechanism used to enhance and present a medical image, according to an embodiment of the invention.

FIG. 3 shows a display diagram illustrating enhancing and presenting a medical image using a corrective mechanism. The image analysis application 106 (executed by the mobile device 104) may process/analyze the digital copy 108 with the CACM 224 to identify the flawed photography effect. In an example scenario, the CACM 224 may process the non-image information 336 and/or the image characteristics information 338 obtained by computer vision analysis tools to identify the flawed photography effect, as previously described.

Furthermore, an orientation information 340 associated with the digital copy 108 may be processed to identify issues associated with an orientation of the digital copy 108. The CACM 224 may enhance the digital copy 108 by re-orienting the digital copy 108 to change a perspective associated with the ROI 109. A change in the perspective associated with the ROI 109 may increase a probability of the CACM 224 to determine the annotation 234.

The CACM 224 may identify the ROI 109 using the AI mechanism. A shape and/or a structure, among other attributes associated with the ROI 109 may be used to determine the annotation 234. The flawed photography effect may also be identified by processing a shape and/or a structure of the ROI 109. The flawed photography effect may be corrected to enhance the ROI 109 with a clearer shape and/or structure. Furthermore, the user may be allowed to provide an input that selects a region of the digital copy 108 as the ROI 109.

In another example scenario, the CACM 224 may identify a glare 344 effect and/or a reflection 346 effect. The glare 344 effect may obscure the digital copy 108 by reducing brightness and/or contrast of the digital copy 108 due to a hotspot caused by a light source (at the time of capture). The CACM 224 may reduce or remove the glare 344 effect to enhance the digital copy 108.

The reflection 346 effect may introduce a reflection of an external entity to the digital copy 108 at the time of capture. The CACM 224 may identify the reflection 346 of the external entity as the flawed photography effect and remove the reflection 346 from the digital copy 108.

The CACM 224 may also identify a moiré pattern 348 as the flawed digital effect within the digital copy 108. The moiré pattern 348 may include round stripe(s) within the digital copy 108. The CACM 224 may remove the moiré pattern to produce the enhanced digital copy 232.

The CACM 224 may further identify a color imbalance 350 as the flawed digital effect within the digital copy 108. The color imbalance 350 may produce a rainbow or a rippling of color on the digital copy 108. The CACM 224 may remove the color imbalance to produce the enhanced digital copy 232.

The CACM 224 may identify a geometric distortion 352 as the flawed digital effect within the digital copy 108. The geometric distortion 352 may be caused by an off axis capture of the digital copy 108. The CACM 224 may re-orient the digital copy 108 to correct the geometric distortion 352.

The CACM 224 may identify a motion blur 354 as the flawed photography effect within the digital copy 108. The motion blur 354 may be caused by a movement of an organ and/or the medical imaging device while capturing the medical image. In addition, motion blur 354 may be caused by patient movement during the image acquisition process. Alternatively, the motion blur 354 may be caused by shaking of a hand of the user capturing the digital copy 108. The CACM 224 may compensate for the motion blur 354 within the digital copy 108 and produce the enhanced digital copy 232.

The CACM 224 may also identify a noise related issue and/or a light exposure 356 issue as the flawed digital effect within the digital copy 108. The CACM 224 may enhance the digital copy 108 to remove and reduce the noise and alleviate the light exposure 356 issue to produce the enhanced digital copy 232.

Furthermore, the CACM 224 may provide a color map 358 of the ROI 109 within the enhanced digital copy 232 as the annotation 234 and/or as part of the annotation 234. The color map 358 may describe probability of a malignancy (of cancer) associated with the ROI 109 and/or section(s) of the ROI 109.

In another example scenario, the CACM 224 may process another digital copy of the medical image in addition to the digital copy 108. Processing of the other digital copy may allow the CACM 224 clarify the ROI 109 by comparing and contrasting the differences between the two copies. The CACM 224 may also process additional digital copies in the analysis procedure to refine the ROI 109.

Figure 4:
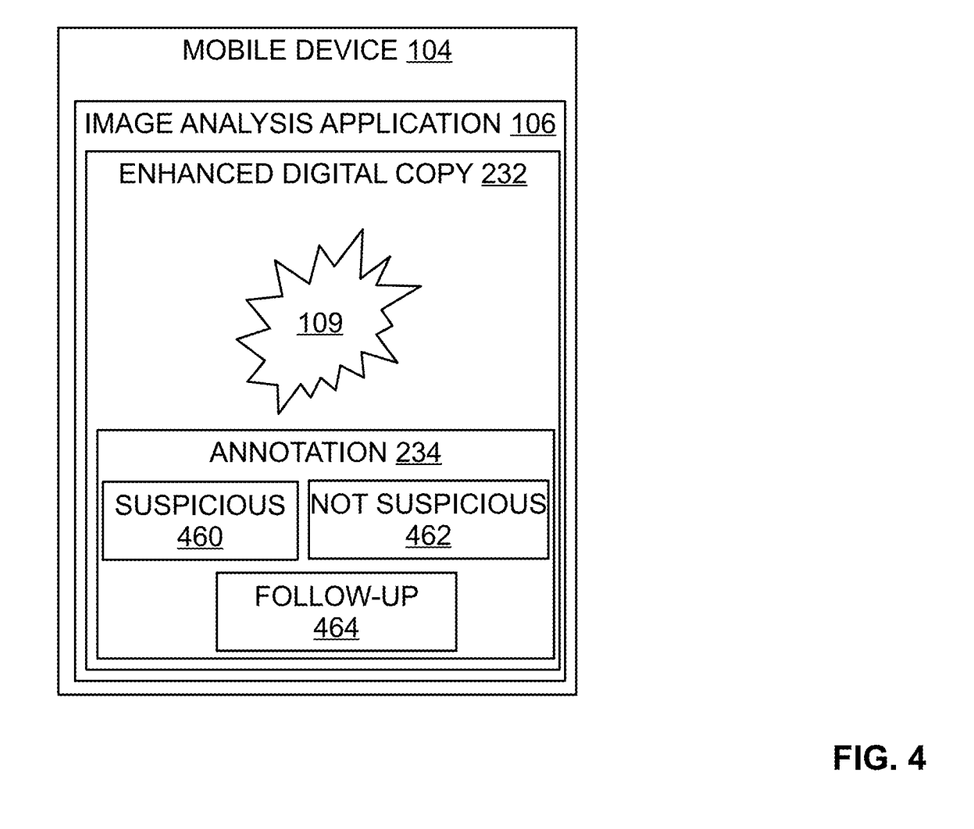
FIG. 4 shows a display diagram illustrating an example of a user experience enhancing and presenting a medical image using a corrective mechanism, according to an embodiment of the invention.

FIG. 4 shows a display diagram illustrating an example of a user experience enhancing and presenting a medical image using a corrective mechanism. In an example scenario, the image analysis application 106 (executed by the mobile device 104) may display an enhanced digital copy 232 of the medical image. The enhanced digital copy 232 may be designated with an annotation 234. The annotation 234 may include a suspicious 460 label. The suspicious 460 label may describe a likelihood of malignancy (of cancer) associated with the ROI 109 in the enhanced digital copy 232. Furthermore, the annotation 234 may include a not suspicious 462 label. The not suspicious 462 label may describe a lack of a malignancy (of cancer) associated with the ROI 109. The annotation 234 may also include a follow up 464 label. The follow up 464 label may describe a necessity to have the enhanced digital copy 232 re-evaluated by a doctor and/or other practitioner to distinguish malignancy related information from the enhanced digital copy 232.

The example scenarios and schemas in FIGS. 1 through 4 are shown with specific components, data types, and configurations. Embodiments are not limited to systems according to these example configurations. A device to enhance and present a medical image using a corrective mechanism may be implemented in configurations employing fewer or additional components in applications and user interfaces. Furthermore, the example schema and components shown in FIGS. 1 through 4 and their subcomponents may be implemented in a similar manner with other values using the principles described herein.

Figure 5:
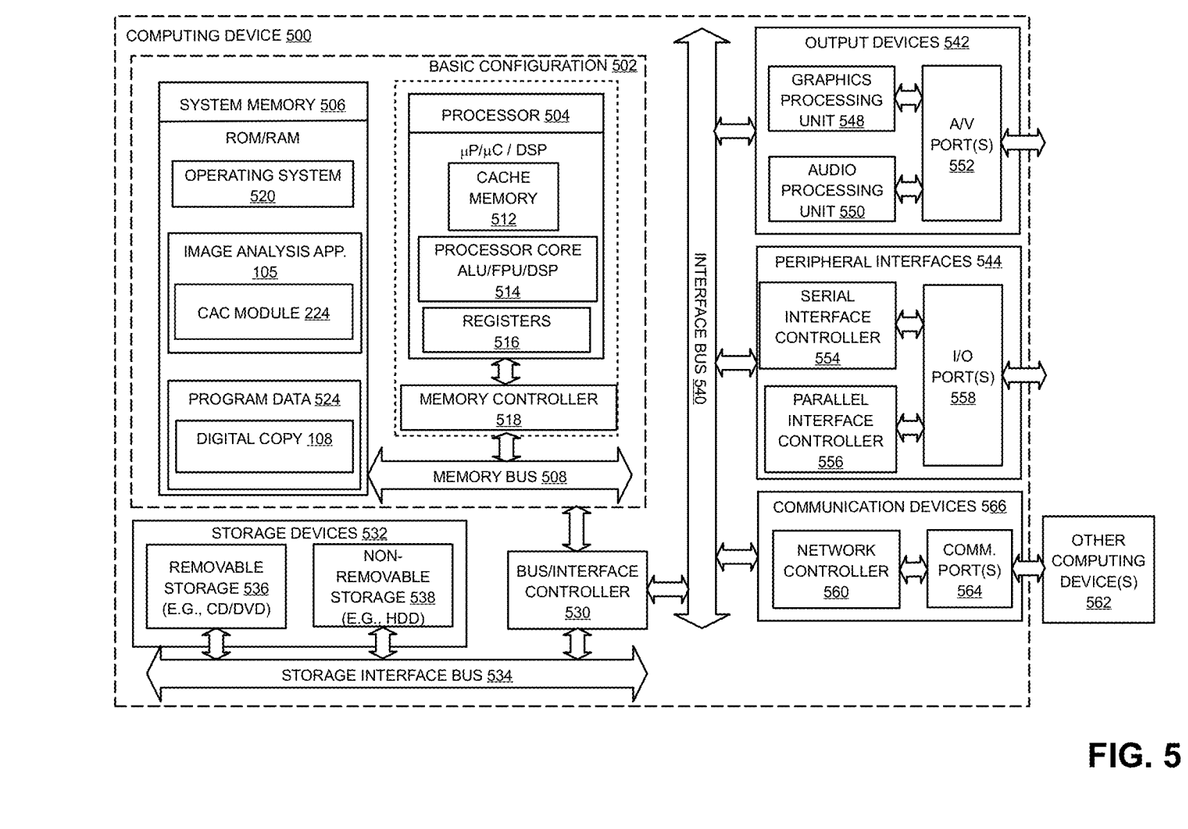
FIG. 5 is a block diagram of an example computing device, which may be used to enhance and present a medical image using a corrective mechanism.

FIG. 5 is a block diagram of an example computing device, which may be used to enhance and provide a medical image using a corrective mechanism, according to embodiments.

For example, computing device 500 may be used as a server, desktop computer, portable computer, smart phone, special purpose computer, or similar device. In a basic configuration 502, the computing device 500 may include one or more processors 504 and a system memory 506. A memory bus 508 may be used for communication between the processor 504 and the system memory 506. The basic configuration 502 may be illustrated in FIG. 5 by those components within the inner dashed line.

Depending on the desired configuration, the processor 504 may be of any type, including but not limited to a microprocessor (µP), a microcontroller (µC), a digital signal processor (DSP), or any combination thereof. The processor 504 may include one more levels of caching, such as a level cache memory 512, one or more processor cores 514, and registers 516. The example processor cores 514 may (each) include an arithmetic logic unit (ALU), a floating-point unit (FPU), a digital signal processing core (DSP Core), a graphics processing unit (GPU), or any combination thereof. An example memory controller 518 may also be used with the processor 504, or in some implementations, the memory controller 518 may be an internal part of the processor 504.

Depending on the desired configuration, the system memory 506 may be of any type including but not limited to volatile memory (such as RAM), non-volatile memory (such as ROM, flash memory, etc.), or any combination thereof. The system memory 506 may include an operating system 520, the image analysis application 106, and a program data 524. The image analysis application 106 may include components such as the CACM 224. The CACM 224 may execute the instructions and processes associated with the image analysis application 106. In an example scenario, the CACM 224 may capture a digital copy of the medical image displayed on a display device. A flawed photography effect associated with the digital copy may be identified by processing the digital copy. Next, the digital copy may be enhanced based on the flawed photography effect. Furthermore, the enhanced digital copy may be processed with an artificial intelligence mechanism to generate an annotation. The annotation may be associated with a cancer identification. In addition, the enhanced digital copy and the annotation may be displayed.

Input to and output out of the image analysis application 106 may be captured and displayed through a display component that may be integrated to the computing device 500. The display component may include a display screen, and/or a display monitor, among others that may capture an input through a touch/gesture based component such as a digitizer. The program data 524 may also include, among other data, the digital copy 108, or the like, as described herein. The digital copy 108 may be enhanced and presented with an annotation associated with a cancer identification, among other things.

The computing device 500 may have additional features or functionality, and additional interfaces to facilitate communications between the basic configuration 502 and any desired devices and interfaces. For example, a bus/interface controller 530 may be used to facilitate communications between the basic configuration 502 and one or more data storage devices 532 via a storage interface bus 534. The data storage devices 532 may be one or more removable storage devices 536, one or more non-removable storage devices 538, or a combination thereof. Examples of the removable storage and the non-removable storage devices may include magnetic disk devices, such as flexible disk drives and hard-disk drives (HDDs), optical disk drives such as compact disk (CD) drives or digital versatile disk (DVD) drives, solid state drives (SSDs), and tape drives, to name a few. Example computer storage media may include volatile and nonvolatile, removable, and non-removable media implemented in any method or technology for storage of information, such as computer-readable instructions, data structures, program modules, or other data.

The system memory 506, the removable storage devices 536 and the non-removable storage devices 538 are examples of computer storage media. Computer storage media includes, but is not limited to, RAM, ROM, EEPROM, flash memory or other memory technology, CD-ROM, digital versatile disks (DVDs), solid state drives, or other optical storage, magnetic cassettes, magnetic tape, magnetic disk storage or other magnetic storage devices, or any other medium which may be used to store the desired information and which may be accessed by the computing device 500. Any such computer storage media may be part of the computing device 500.

The computing device 500 may also include an interface bus 540 for facilitating communication from various interface devices (for example, one or more output devices 542, one or more peripheral interfaces 544, and one or more communication devices 566) to the basic configuration 502 via the bus/interface controller 530. Some of the example output devices 542 include a graphics processing unit 548 and an audio processing unit 550, which may be configured to communicate to various external devices such as a display or speakers via one or more A/V ports 552. One or more example peripheral interfaces 544 may include a serial interface controller 554 or a parallel interface controller 556, which may be configured to communicate with external devices such as input devices (for example, keyboard, mouse, pen, voice input device, touch input device, etc.) or other peripheral devices (for example, printer, scanner, etc.) via one or more I/O ports 558. An example of the communication device(s) 566 includes a network controller 560, which may be arranged to facilitate communications with one or more other computing devices 562 over a network communication link via one or more communication ports 564. The one or more other computing devices 562 may include servers, computing devices, and comparable devices.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

The computing device 500 may be implemented as a part of a specialized server, mainframe, or similar computer, which includes any of the above functions. The computing device 500 may also be implemented as a personal computer including both laptop computer and non-laptop computer configurations. Additionally, the computing device 500 may include specialized hardware such as an application-specific integrated circuit (ASIC), a field programmable gate array (FPGA), a programmable logic device (PLD), and/or a free form logic on an integrated circuit (IC), among others.

Example embodiments may also include methods to enhance and present a medical image using a corrective mechanism. These methods can be implemented in any number of ways, including the structures described herein. One such way may be by machine operations, of devices of the type described in the present disclosure. Another optional way may be for one or more of the individual operations of the methods to be performed in conjunction with one or more human operators performing some of the operations while other operations may be performed by machines. These human operators need not be collocated with each other, but each can be only with a machine that performs a portion of the program. In other embodiments, the human interaction can be automated such as by preselected criteria that may be machine automated.

Figure 6:
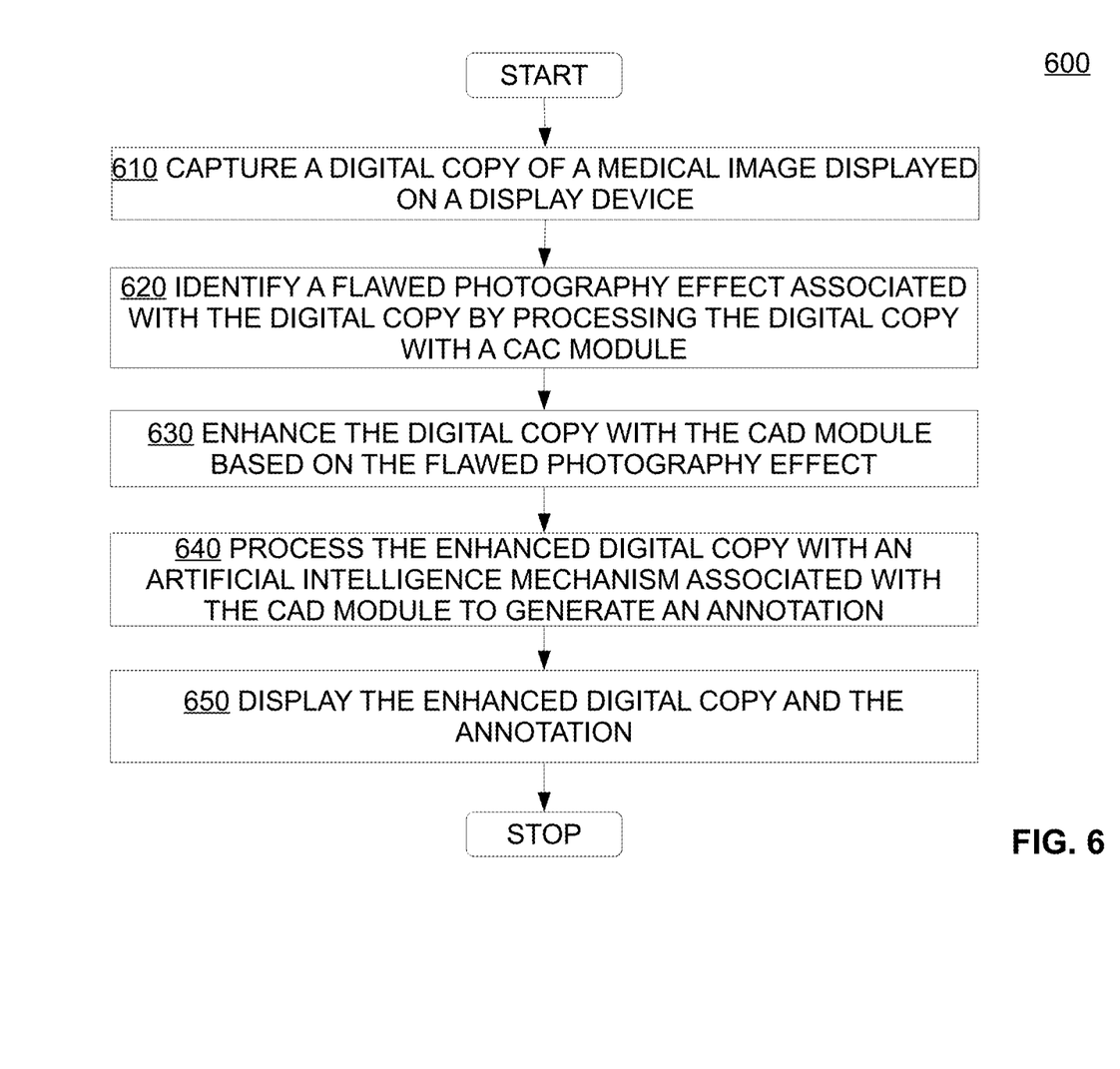
FIG. 6 is a logic flow diagram illustrating a process for enhancing and presenting a medical image using a corrective mechanism, according to an embodiment of the invention.

FIG. 6 is a logic flow diagram illustrating a process for enhancing and presenting a medical image using a corrective mechanism. Process 600 may be implemented on a computing device, such as the computing device 500 or another system.

Process 600 begins with operation 610, where an image analysis application may capture a digital copy of the medical image displayed on a display device. The medical image may include an x-ray, a CT, an ultrasound, and/or a PET scan. At operation 620, a flawed photography effect associated with the digital copy may be identified by processing the digital copy. Next, at operation 630, the digital copy may be enhanced based on the flawed photography effect.

Furthermore, at operation 640, the enhanced digital copy may be processed with an artificial intelligence mechanism to generate an annotation. The annotation may designate a suspicious, a not suspicious, or a follow up label associated with a cancer identification. At operation 650, the enhanced digital copy and the annotation may be displayed.

The operations included in process 600 is for illustration purposes. Enhancing and presenting a medical image using a corrective mechanism may be implemented by similar processes with fewer or additional steps, as well as in different order of operations using the principles described herein. The operations described herein may be executed by one or more processors operated on one or more computing devices, one or more processor cores, specialized processing devices, and/or special purpose processors, among other examples.

A method of enhancing and presenting a medical image using a corrective mechanism is also described. The method includes receiving a digital copy of the medical image from an image source. Next, a flawed photography effect associated with the digital copy may be identified by processing the digital copy. The digital copy may be enhanced based on the flawed photography effect. Furthermore, the digital copy may be processed with an artificial intelligence mechanism to generate an annotation, The annotation may include a suspicious label, a not suspicious label, and/or a follow-up label associated with a cancer identification. The digital copy and the annotation may next be provided for a presentation.

When introducing elements of the present disclosure or the embodiment(s) thereof, the articles "a," "an," and "the"

are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A device to enhance and present a medical image using a corrective mechanism, wherein the device performs one or more operations comprising:
   receiving a digital copy from a camera, wherein the camera captured the digital copy of the medical image displayed on a monitor, and wherein the monitor is external to the camera;
   identifying a flawed photography effect associated with the digital copy by processing the digital copy using a deep learning mechanism performed by a computer analysis and correction module (CACM);
   enhancing the digital copy using the deep learning mechanism performed by the CACM based on the flawed photography effect;
   processing the enhanced digital copy using the deep learning mechanism performed by the CACM to generate an annotation, wherein the annotation is associated with a cancer identification; and
   displaying one or more of the enhanced digital copy and the annotation overlaid by an augmented reality mechanism on to the monitor displaying the medical image.

2. The device of claim 1, wherein
   the camera includes a polarizer to reduce one or more of a reflection effect and a glare effect associated with capturing the digital copy of the medical image.

3. The device of claim 1, wherein the device performs one or more additional operations comprising:
   analyzing one or more non-image information associated with the digital copy and the camera using the deep learning mechanism performed by the CACM, wherein the non-image information includes one or more of a flash information, a focal length, a shutter speed, a camera model information, an aperture setting, and a capture date and time information;
   identifying the flawed digital effect from the one or more analyzed non-image information using the deep learning mechanism performed by the CACM; and
   enhancing the digital copy to correct the flawed digital effect using the deep learning mechanism performed by the CACM.

4. The device of claim 1, wherein the device performs one or more additional operations comprising:
   analyzing one or more image characteristic information associated with the digital copy using the deep learning mechanism performed by the CACM, wherein the one or more characteristic information includes an orientation, a red-eye detection, a blur, a color balance, an exposure, and a noise information;
   identifying the flawed digital effect from the one or more analyzed characteristic information using the deep learning mechanism performed by the CACM; and
   enhancing the digital copy to correct the flawed digital effect using the deep learning mechanism performed by the CACM.

5. The device of claim 1, wherein the mobile device performs one or more additional operations comprising:
   identifying a region of interest (ROI) within the digital copy automatically using the deep learning mechanism performed by the CACM; and
   processing the ROI to identify the flawed photography effect using the deep learning mechanism performed by the CACM.

6. The device of claim 1, wherein the mobile device performs one or more additional operations comprising:
   receiving a selection of a region of interest (ROI) within the digital copy from a user using the deep learning mechanism performed by the CACM; and
   processing the ROI to identify the flawed photography effect using the deep learning mechanism performed by the CACM.

7. The device of claim 1, wherein the mobile device performs one or more additional operations comprising:
   identifying a glare effect within the digital copy as the flawed photography effect using the deep learning mechanism performed by the CACM; and
   enhancing the digital copy to correct the flawed photography effect using the deep learning mechanism performed by the CACM.

8. The device of claim 1, wherein the mobile device performs one or more additional operations comprising:
   identifying a reflection effect within the digital copy as the flawed photography effect using the deep learning mechanism performed by the CACM; and
   enhancing the digital copy to correct the flawed photography effect using the deep learning mechanism performed by the CACM.

9. The device of claim 1, wherein the mobile device performs one or more additional operations comprising:
   identifying a moiré pattern within the digital copy as the flawed photography effect using the deep learning mechanism performed by the CACM; and
   enhancing the digital copy to correct the flawed photography effect using the deep learning mechanism performed by the CACM.

10. The device of claim 1, wherein the mobile device performs one or more additional operations comprising:
    identifying a geometric distortion within the digital copy as the flawed photography effect using the deep learning mechanism performed by the CACM; and
    enhancing the digital copy to correct the flawed photography effect using the deep learning mechanism performed by the CACM.

11. The device of claim 1, wherein the mobile device performs one or more additional operations comprising:
    identifying a noise within the digital copy as the flawed photography effect using the deep learning mechanism performed by the CACM; and
    enhancing the digital copy to correct the flawed photography effect using the deep learning mechanism performed by the CACM.

12. The device of claim 1, wherein the mobile device performs one or more additional operations comprising:
    identifying a light exposure issue as the flawed photography effect using the deep learning mechanism performed by the CACM; and
    enhancing the digital copy to correct the flawed photography effect using the deep learning mechanism performed by the CACM.

13. The device of claim 1, wherein the mobile device performs one or more additional operations comprising:

providing a color map of a region of interest (ROI) within the digital copy as the annotation using the deep learning mechanism performed by the CACM, wherein the color map describes a probability of a malignancy associated with the ROI.

14. The device of claim 1, wherein the mobile device performs one or more additional operations comprising:
   identifying a motion blur as the flawed photography effect using the deep learning mechanism performed by the CACM; and
   enhancing the digital copy to correct the flawed photography effect using the deep learning mechanism performed by the CACM.

15. A mobile device for enhancing and presenting a medical image using a corrective mechanism, the mobile device comprising:
   a display component configured to accept an input and display an output associated with an image analysis application,
   a camera component configured to capture a first digital copy of the medical image displayed on a monitor in relation to the image analysis application, wherein the camera component is external to the monitor,
   a memory configured to store instructions associated with the image analysis application,
   a processor coupled to the display component, the camera component, and the memory, the processor executing the instructions associated with the image analysis application, wherein the image analysis application includes:
      a computer analysis and correction module (CACM) performing one or more operations comprising:
         receiving a first digital copy of the medical image from the camera component;
         identifying a flawed photography effect associated with the first digital copy by processing the first digital copy using a deep learning mechanism;
         enhancing the first digital copy based on the flawed photography effect using the deep learning mechanism;
         processing the first digital copy using the deep learning mechanism to generate an annotation, wherein the annotation includes one of a suspicious label, a not suspicious label, and a follow-up label associated with a cancer identification; and
         displaying the first digital copy and the annotation overlaid by an augmented reality mechanism on to the monitor displaying the medical image.

16. The mobile device of claim 15, wherein the medical image includes one of an ultrasound scan, a x-ray scan, a magnetic resonance imaging (MRI) scan, a computed tomography (CT) scan, and a positron emission tomography (PET) scan.

17. The mobile device of claim 15, wherein the flawed photography effect is identified by processing a second digital copy of the medical image using the deep learning mechanism, wherein the second digital copy is received from the camera component.

18. A method of enhancing and presenting a medical image using a corrective mechanism, the method comprising:
   receiving a digital copy of the medical image displayed on a monitor, wherein the digital copy is captured by an image source, wherein the monitor is external to the image source;
   identifying a flawed photography effect associated with the digital copy by processing the digital copy using a deep learning mechanism;
   enhancing the digital copy based on the flawed photography effect using the deep learning mechanism;
   processing the digital copy using the deep learning mechanism to generate an annotation, wherein the annotation includes one of a suspicious label, a not suspicious label, and a follow-up label associated with a cancer identification; and
   providing the digital copy and the annotation for a presentation overlaid by an augmented reality mechanism on to the monitor displaying the medical image.

* * * * *